US00PP28960P2

(12) United States Plant Patent
Brown

(10) Patent No.: US PP28,960 P2
(45) Date of Patent: Feb. 13, 2018

(54) ***LAGERSTROEMIA* PLANT NAMED 'SB 2011-20'**

(50) Latin Name: *Lagerstroemia indica*
Varietal Denomination: SB 2011-20

(71) Applicant: Stanley Allen Brown, Clarksville, AR (US)

(72) Inventor: Stanley Allen Brown, Clarksville, AR (US)

( * ) Notice: Subject to any disclaimer, the term of this patent is extended or adjusted under 35 U.S.C. 154(b) by 2 days.

(21) Appl. No.: 14/999,863

(22) Filed: Jul. 11, 2016

(51) Int. Cl.
*A01H 5/00* (2006.01)

(52) U.S. Cl.
USPC ..... Plt./252

(58) Field of Classification Search
USPC ..... Plt./226, 252
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Lagerstroemia* plant named 'SB 2011-20' that is characterized by its low growing and wide spreading plant habit, its low seed set, its extended bloom period of bright red flowers, its high resistance to powdery mildew, and its good frost resistance.

2 Drawing Sheets

Botanical classification: *Lagerstroemia indica.*
Variety denomination: 'SB 2011-20'.

BACKGROUND OF THE INVENTION

The present invention relates to a new and distinct cultivar of *Lagerstroemia indica*. The new *Lagerstroemia* will hereafter by its cultivar name, 'SB 2011-20'. 'SB 2011-20' is a new cultivar of deciduous shrub grown for use as an ornamental landscape plant.

The objectives of the breeding program are to develop new cultivars of *Lagerstroemia* with low growing and spreading plant habits with good disease resistance and strong flower colors.

The new cultivar of *Lagerstroemia* is the result of a controlled breeding program conducted by the Inventor in Clarksville, Ark. The Inventor made a controlled cross in 2010 between unnamed and unpatented plants of *Lagerstroemia* from his breeding program; ref. no. 2009-3 as the female parent and ref. no. 2009-15 as the male parent. 'SB 2011-20' was selected in 2011 as a single unique plant amongst the resulting seedlings.

Asexual propagation of the new cultivar was first accomplished by the Inventor using stem cuttings in 2012 in Clarksville, Ark. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SB 2011-20' as a unique cultivar of *Lagerstroemia.*

1. 'SB 2011-20' exhibits a low growing and wide spreading plant habit.
2. 'SB 2011-20' exhibits a low seed set.

3. 'SB 2011-20' exhibits blooms over an extended time period.
4. 'SB 2011-20' exhibits high resistance to powdery mildew.
5. 'SB 2011-20' exhibits bright red flowers.

The female parent of 'SB 2011-20', ref. no. 2009-3, differs from 'SB 2011-20' in having a taller and more upright plant habit and in having better seed set. The male parent of 'SB 2011-20', ref. no. 2009-15, differs from 'SB 2011-20' in having a taller plant habit and in having flowers that are pinker in color. 'SB 2011-20' can also be most closely compared to the *Lagerstroemia* cultivars 'Sacramento' (not patented) and 'Rosey Carpet' (U.S. Plant Pat. No. 13,965). Both cultivars are similar to 'SB 2011-20', in having a spreading plant habit. 'Sacramento' differs from 'SB 2011-20', in having a taller plant habit, in having flowers that are lighter red in color and in being less disease resistant. 'Rosey Carpet' differs from 'SB 2011-20', in having flowers that are pinker in color and in being less disease resistant.

BRIEF DESCRIPTION OF THE DRAWINGS

The accompanying colored photographs illustrate the overall appearance and distinct characteristics of the new *Lagerstroemia*. The photographs were taken of a plant three years in age as grown outdoors in a 2-gallon container in Clarksville, Ark.

The photograph in FIG. 1 provides a side view of 'SB 2011-20' in bloom.

Figure 1:
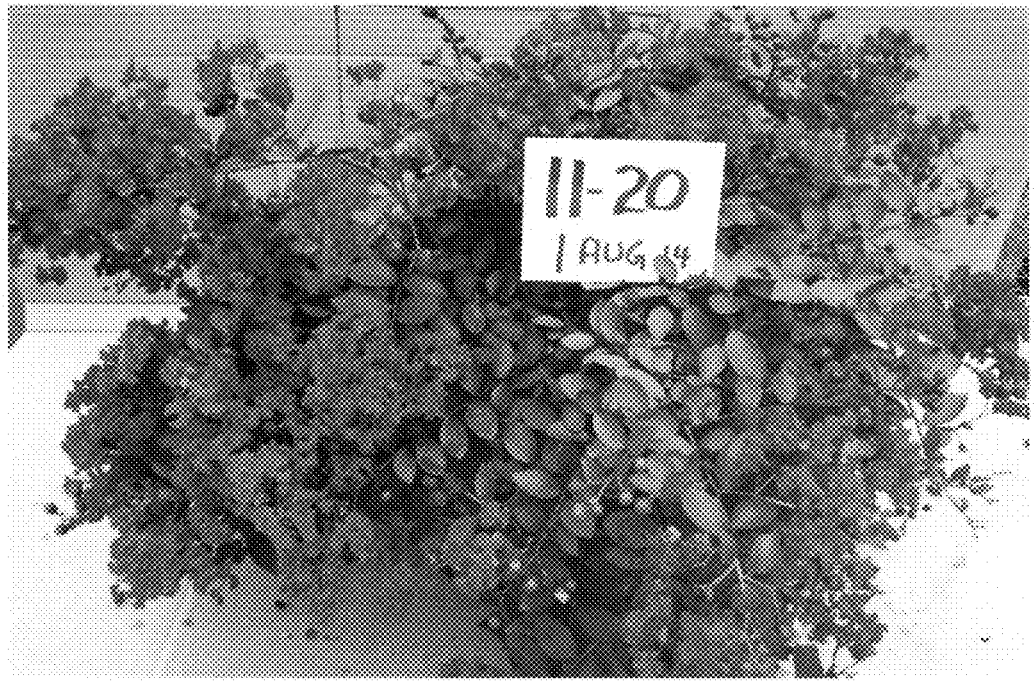
Figure 2:
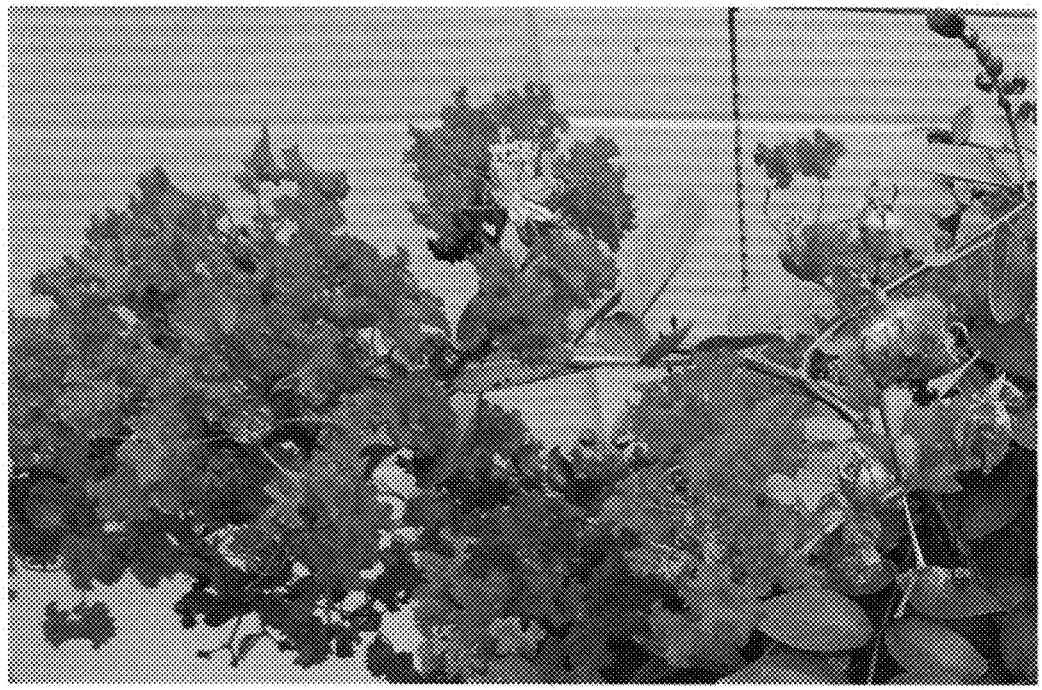

The photograph in FIG. 2 provides a close-up view of the inflorescences of 'SB 2011-20'.

The colors in the photographs are as close as possible with the digital photography techniques available and the color values cited in the detailed botanical description accurately describe the colors of the new *Lagerstroemia.*

DETAILED BOTANICAL DESCRIPTION

The descriptions were taken of plants one year in age as grown outdoors in 3-quart containers in Clarksville, Ark.

The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Long blooming; blooming July into September.

*Plant type*.—Deciduous shrub.

*Plant habit*.—Low growing and wide spreading.

*Height and spread*.—Reaches an average of 50 cm in height and 100 cm in spread as a three year-old plant in the landscape.

*Cold hardiness*.—At least to U.S.D.A. Zone 7.

*Diseases*.—Highly resistant to powdery mildew (*Erysiphe lagerstroemia*) and good resistance to leaf spot (*Phyllosticta* spp.).

*Root description*.—Fibrous and fine, 199D in color.

*Root development*.—Roots in 6 weeks and fully develops in a 9-cm container in about 4 months.

*Propagation*.—Stem cuttings.

*Growth rate*.—Moderate.

Stem description:

*Shape*.—New growth quadrangulate, mature stems oval.

*Stem color*.—New growth; 183D in color on sunny exposed side and 146D on lower shaded side, mature stems; 145B covered with fissured bark closest to 164A.

*Stem size*.—Lateral branches; an average of 17 cm in length and 4 mm in diameter, secondary stems; an average of 20 cm in length and 2.5 mm in diameter, tertiary stems; an average of 20 cm in length and 2.5 mm in diameter.

*Stem surface*.—Young stems; slightly pubescent, mature stem; fissured bark with some peeling.

*Stem strength*.—Strong.

*Branch angle*.—Lateral stems held at about a 30° angle (0° horizontal), secondary and tertiary stems stems held at about a 30° angle to lateral stems.

*Branching*.—2 lateral branches with 7 secondary branches per lateral branch and 2 to 5 tertiary branches per main stem.

*Internode length*.—An average of 1 cm.

Foliage description:

*Leaf shape*.—Elliptic.

*Leaf division*.—Single.

*Leaf base*.—Cuneate.

*Leaf apex*.—Rounded to broadly acute.

*Leaf venation*.—Pinnate, not conspicuous, color; upper surface 1138A, lower surface 138C.

*Leaf margins*.—Entire.

*Leaf arrangement*.—Opposite to nearly opposite.

*Leaf attachment*.—Short petiolate.

*Leaf surface*.—Both surfaces dull and glabrous.

*Leaf size*.—An average of 3.5 cm in length and 2.3 cm in width.

*Leaf quantity*.—An average of 20 (10 pairs) per branch 17 cm in length.

*Leaf color*.—New growth upper and lower surface (growth tips); a blend of 147B and 147C and slightly suffused with 187C, young and mature leaves upper surface; 137A, young and mature growth lower surface; 138B.

*Leaf fragrance*.—Fragrance typical for *Lagerstroemia* detected when touched.

*Petioles*.—An average of 1 mm in length and width and 138B in color, slightly pubescent surface, strong and stout.

Flower description:

*Inflorescence type*.—Terminal thyrse on secondary branches.

*Lastingness of inflorescence*.—About one week.

*Inflorescence size*.—An average of 8 cm in height and width.

*Inflorescence number*.—An average of 4 per lateral stem.

*Flower number*.—Up to 24 flowers per inflorescence.

*Flower fragrance*.—Faint.

*Flower buds*.—Flattened globular in shape, an average of 8 mm in diameter and 7 mm in depth, surface; glabrous and satiny, color; a blend 187B and 181B with sepal margins 187B.

*Flower aspect*.—Upright to outward.

*Flower type*.—Rotate.

*Flower size*.—An average of 3.5 cm in diameter and 2 cm in depth.

*Petals*.—An average of 6, roughly ovate in shape and very ruffled, strongly undulate bidentate and crisped margins, stalked base, rounded apex, both surfaces glabrous and dull, an average of 2.2 cm in length and 1.4 cm in width with stalk portion 7 mm in length and 1 mm in width, color when opening and when fully open upper and lower surface; a blend of 64A and 64B with stalk 71A, petal color does not fade.

*Calyx*.—Campanulate in shape, an average of 8 mm in length and diameter.

*Sepals*.—5, lower ⅔ fused, free portion; triangular in shape, 4 mm in depth and width, entire margins, acute apex with mucronate tip, both surfaces are smooth and slightly satiny, color; upper and lower surface when opening and when fully open a blend 187B and 181B with margins 187B.

*Peduncles*.—Strong, main peduncle (rachis); an average of 5 cm in length and 1.5 mm in width, secondary peduncles; an average of 1.5 cm in length and 1.2 mm in width, 183D in color on sunny exposed side and 146D on lower shaded side, surface is slightly pubescent, main peduncles held at an average angle of 0° to the secondary branch, secondary peduncles held at an average angle of 45° to the main peduncle.

*Pedicels*.—Strong, an average of 4.5 mm in length and 1 mm in width, a blend of 183D and 146D in color, held at an average angle of 0° to 15° to secondary peduncle (0° vertical), satiny and very slightly pubescent surface.

Reproductive organs:

*Stamens*.—An average of 6 antesepalous and 25 antepetalous, anther (observed on about ⅔ of stamens); an average of 1.5 mm in length, dorsifixed, narrow oblong in shape, 165B in color, pollen abundant in quantity and 21B in color, filament; antesepalous; an average of 1.5 cm in length and 187D in color, filaments antepelalous; an average of 8 mm in length, very fine, and 65C in color.

*Pistils*.—An average of 1, an average of 1.7 cm in length, style; an average of 1.6 cm in length and 187D in color, stigma is club-shaped and 147A in color, ovary is oblong-globose in shape, 3 mm in length and 2.5 mm in width, and 160B in color.

*Seed and fruit*.—Very low seed set has been observed and no seeds where observed on plants used for data collection.

It is claimed:

1. A new and distinct cultivar of *Lagerstroemia* plant named 'SB 2011-20' as herein illustrated and described.

* * * * *